US012782352B2

(12) United States Patent
Yamashita et al.

(10) Patent No.: US 12,782,352 B2
(45) Date of Patent: Nov. 3, 2026

(54) ALLERGEN-IMMOBILIZED CARRIER AND METHOD OF DETECTING ALLERGEN-SPECIFIC ANTIBODY

(71) Applicant: Toray Industries, Inc., Tokyo (JP)

(72) Inventors: Kazumi Yamashita, Kamakura (JP); Masateru Ito, Kamakura (JP); Yoichiro Koshi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 657 days.

(21) Appl. No.: 18/271,493

(22) PCT Filed: Jan. 20, 2022

(86) PCT No.: PCT/JP2022/001905
§ 371 (c)(1),
(2) Date: Jul. 10, 2023

(87) PCT Pub. No.: WO2022/158509
PCT Pub. Date: Jul. 28, 2022

(65) Prior Publication Data

US 2024/0060976 A1 Feb. 22, 2024

(30) Foreign Application Priority Data

Jan. 21, 2021 (JP) ................................ 2021-007775

(51) Int. Cl.
*G01N 33/543* (2006.01)
*G01N 33/564* (2006.01)
*G01N 33/68* (2006.01)

(52) U.S. Cl.
CPC ..... *G01N 33/564* (2013.01); *G01N 33/54353* (2013.01); *G01N 33/686* (2013.01)

(58) Field of Classification Search
None
See application file for complete search history.

(56) References Cited

U.S. PATENT DOCUMENTS

2004/0071596 A1 4/2004 Innerst et al.
2004/0241883 A1 12/2004 Tanga et al.
(Continued)

FOREIGN PATENT DOCUMENTS

EP 3505934 A1 * 7/2019
JP 2000-266746 A 9/2000
(Continued)

OTHER PUBLICATIONS

Jean Bousquet, MD et al., "Comparison between RAST and Pharmacia CAP system: A new automated specific IgE assay," The Journal of Allergy and Clinical Immunology, vol. 85, No. 6, pp. 1039-1043 (1990).

(Continued)

*Primary Examiner* — Rebecca M Giere
(74) *Attorney, Agent, or Firm* — DLA Piper LLP (US)

(57) ABSTRACT

An allergen-immobilized carrier is for use in allergy testing, which carrier is capable of simultaneously measuring multiple items of allergen-specific IgE antibodies with a high sensitivity even when the amount of sample smaller than that used conventionally is used, and capable of performing the measurement with a high correlation with the measured values obtained using "ImmunoCAP." The carrier is an allergen-immobilized carrier for use in allergy testing, characterized in that the allergen(s) is/are immobilized on the carrier at a density of from 120 to 500 ng/$cm^2$.

13 Claims, 1 Drawing Sheet

(56) References Cited

U.S. PATENT DOCUMENTS

| | | | |
|---|---|---|---|
| 2009/0111702 A1 | 4/2009 | Sampson et al. | |
| 2011/0275095 A1 | 11/2011 | Babson | |
| 2015/0316546 A1 | 11/2015 | Oka et al. | |
| 2019/0079083 A1* | 3/2019 | Harwanegg | G01N 33/54346 |
| 2019/0086324 A1 | 3/2019 | Marrinucci et al. | |

FOREIGN PATENT DOCUMENTS

| | | | |
|---|---|---|---|
| JP | 2001-281249 | A | 10/2001 |
| JP | 2002-350447 | A | 12/2002 |
| JP | 2004-264289 | A | 9/2004 |
| JP | 2006-267058 | A | 10/2006 |
| JP | 2010-014669 | A | 1/2010 |
| JP | 2011-013000 | A | 1/2011 |
| JP | 4829460 | B2 | 9/2011 |
| JP | 2012-163491 | A | 8/2012 |
| JP | 5322242 | B2 | 10/2013 |
| JP | 2020-132803 | A | 8/2020 |
| JP | 2021-148610 | A | 9/2021 |
| WO | 2014/097558 | A1 | 6/2014 |
| WO | 2021/015123 | A1 | 1/2021 |
| WO | 2021/187398 | A1 | 9/2021 |

OTHER PUBLICATIONS

Nava Levit-Binnun et al., "Quantitative Detection of Protein Arrays," Analytical Chemistry, vol. 75, No. 6, pp. 1436-1441 (2003).

International Search Report dated Apr. 12, 2022 in counterpart International Application No. PCT/JP2022/001905 w/English translation.

Written Opinion dated Apr. 12, 2022 in counterpart International Application No. PCT/JP2022/001905.

Office Action dated Mar. 13, 2025, from counterpart Taiwanese Application No. 111102147.

Lehrer, S.B. et al.. "Enhancement of murine IgE antibody detection by IgG removal," Journal of Immunological Methods, Jan. 2004, vol. 284. pp. 1-6.

Partial Extended European Search Report dated Oct. 7, 2024, from counterpart European Patent Application No. 22 74 2631.

Partial European Search Opinion dated Oct. 7, 2024, from counterpart European Patent Application No. 22 74 2631.

Popsecu, F-D. et al., "Precision medicine allergy immunoassay methods for assessing immunoglobulin E sensitization to aeroallergen molecules," *World Journal of Methodology*, vol. 8, No. 3, Nov. 29, 2018, pp. 17-36.

Breitweiser, A et al.: "A novel dipstick developed for rapid Bet v 1-specific IgE detection: recombinant allergen immobilized via a monoclonal antibody to crystlline bacterial cell-surface layers," *Allergy*, Wiley-Blackwell Publishing Ltd, United Kingdom, vol. 53, No. 8, Aug. 1, 1998 (Aug. 1, 1998), pp. 786-793—Abstract only.

Hyunjin, J.et al.: "Allergen Microarrays for In Vitro Diagnostics of Allergies: Comparison with ImmunoCAP and AdvanSure," *Annals of Laboratory Medicine*, vol. 38, No. 4, Jul. 28, 2018, pp. 338-347.

Office Action dated May 10, 2026, from counterpart Chinese Application No. 202280010366.X.

Office Action dated Mar. 31, 2026, from counterpart Japanese Application No. 2022-505257.

* cited by examiner

ALLERGEN-IMMOBILIZED CARRIER AND METHOD OF DETECTING ALLERGEN-SPECIFIC ANTIBODY

TECHNICAL FIELD

This disclosure relates to a carrier on which an allergen for detecting an allergen-specific antibody is immobilized, and a method of detecting an allergen-specific antibody using the carrier.

BACKGROUND

Allergy testing is usually performed by measuring the amount of an allergen-specific IgE antibody present in the blood or tear fluid of a subject. In the blood or tear fluid of a subject who experiences a stronger allergic reaction to a specific allergen, a larger amount of an IgE antibody specific to the allergen is present, and thus results in a higher measured value of the antibody.

Detection of a specific IgE antibody has been carried out by: preparing an allergen-immobilized carrier on which the allergen is immobilized; bringing a sample into contact with the carrier to allow a reaction to occur, thereby capturing the specific IgE antibody in the sample which binds to the allergen; and detecting the thus-formed complex of the allergen and the specific antibody, using an enzyme or a fluorescent-labeled anti-IgE antibody.

ELISA (Enzyme-Linked Immunosorbent Assay) is known as a representative method of measuring a substance to be tested, using a carrier on which a protein such as an allergen or the like is immobilized, and a carrier in which a protein is immobilized on a polystyrene carrier is generally used. For example, JP 2000-266746 A discloses a technique that measures milk-specific IgE antibody in a patient with milk allergy by ELISA. JP 4829460 B discloses a technique that immobilizes an allergen on a polystyrene carrier.

Further, Nava Levit-Binnun et al., Anal Chem., 75(6): 1436-41 (2003) discloses a detection technique using a microarray in which a protein is immobilized on a glass carrier. In addition, Jean Bousquet et al., J. Allergy Clin. Immunol., 85(6): 1039-1043 (1990), JP 5322242 B and JP 2020-132803 A disclose detection techniques using a carrier in which an allergen is immobilized on a porous cellulose sponge, a carrier in which an allergen is immobilized on DLC (Diamond-like Carbon) and a carrier in which an allergen is immobilized on a photoreactive resin, respectively.

In the clinical practice of allergy testing, "ImmunoCAP" (registered trademark) manufactured by Thermofisher Diagnostics Ltd., which is disclosed in Jean Bousquet et al. and in which an allergen is immobilized on a porous cellulose sponge, is standardly used in the measurement of specific IgE antibodies. Determining a treatment plan for an allergy, conducting a food challenge test or determining the acquisition of allergy tolerance has been performed with reference to the measured values (hereinafter, also referred to as "ImmunoCAP values") obtained using the "ImmunoCAP" and a probability curve (a curve indicating the relationship between the "ImmunoCAP values" and the probability of allergy symptoms being induced). Since "ImmunoCAP" is standardly used in the diagnosis of allergy testing, as described above, having a good correlation with the "ImmunoCAP values" is essential in the development of a novel test drug for measuring a specific IgE antibody.

On the other hand, "ImmunoCAP" is a product which allows for measuring an allergen-specific IgE antibody against only one item of allergen per one testing. Since 40 microliters of serum is required for one measurement, it is necessary to draw several milliliters of blood to measure a plurality of items of allergen-specific IgE antibodies. Many of the allergy patients who are the subjects to be tested are children, and drawing several milliliters of blood from a very small child or puncturing an extremely narrow blood vessel of a child with a needle imposes a heavy physical burden. Therefore, it is difficult to perform simultaneous testing of multiple items of allergen-specific IgE antibodies, using "ImmunoCAP."

In view of such circumstances, the development of an allergen-immobilized carrier is desired, which is capable of measuring multiple items of allergen-specific IgE antibodies using a small amount of blood (about 100 μL or less of blood, which corresponds to one drop of blood) with a high sensitivity and with a high correlation with the measured ImmunoCAP values.

SUMMARY

We found out that the use of a carrier on which an allergen(s) is/are immobilized at a density of from 120 to 500 ng/cm$^2$ enables performing simultaneous measurements of multiple items of allergens, with a high sensitivity and with a high correlation with "ImmunoCAP."

We thus provide:

(1) An allergen-immobilized carrier for detecting an allergen-specific antibody, wherein the carrier includes an allergen-immobilization region on which the allergen is immobilized; and wherein the allergen is immobilized at a density of 120 ng/cm$^2$ or more and 500 ng/cm$^2$ or less.

(2) The allergen-immobilized carrier of (1), wherein the allergen is immobilized at a density of 180 ng/cm$^2$ or more and 300 ng/cm$^2$ or less.

(3) The allergen-immobilized carrier of (1) or (2), wherein the carrier includes a protrusion provided thereon, and the protrusion is the allergen-immobilization region.

(4) The allergen-immobilized carrier of any one of (1) to (3), wherein two or more and 100 or less types of allergens are immobilized on the allergen-immobilization regions.

(5) The allergen-immobilized carrier of any one of (1) to (4), wherein the allergen(s) is/are immobilized via a polymer including a unit represented by formula (Ia) or (Ib):

(Ia)

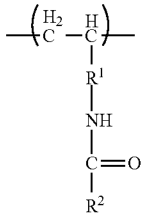

-continued (Ib)

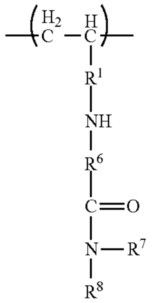

wherein, in formula (Ia) and formula (Ib), $R^1$ represents an alkylene group having from 1 to 4 carbon atoms; $R^2$ represents $R^3$, $OR^4$ or $NHR^5$, wherein each of $R^3$ and $R^5$ independently represents a hydrogen atom or an alkyl group having from 1 to 4 carbon atoms, and $R^4$ represents an alkyl group having from 1 to 4 carbon atoms; $R^6$ represents an alkylene group having from 1 to 2 carbon atoms; and each of $R^7$ and $R^8$ independently represents a hydrogen atom or an alkyl group having from 1 to 4 carbon atoms.

(6) The allergen-immobilized carrier of (3), wherein the carrier includes a reaction vessel including the protrusion provided thereon.

(7) The allergen-immobilized carrier of any one of (1) to (6), wherein at least one of the allergen(s) is egg white, milk, peanut or mite.

(8) The allergen-immobilized carrier of any one of (1) to (7), wherein the carrier is made of a resin containing an aliphatic structure.

(9) The allergen-immobilized carrier of any one of (1) to (8), wherein the carrier is made of a resin containing an ester.

(10) The allergen-immobilized carrier of any one of (1) to (9), wherein the carrier is made of an acrylic resin.

(11) The allergen-immobilized carrier of any one of (1) to (10), wherein the carrier is made of a polyacrylate or a polymethacrylate.

(12) A method of detecting an allergen-specific antibody, the method including the steps of:

bringing a sample into contact with the allergen-immobilized carrier of any one of (1) to (11), to form a complex of the allergen, and of an IgE antibody specific to the allergen contained in the sample; and detecting the thus formed complex of the allergen and the allergen-specific IgE antibody.

(13) The method of detecting an allergen-specific antibody of (12), wherein the sample is a sample from which at least one type of antibody selected from the group consisting of IgG antibody, IgM antibody, IgA antibody and IgD antibody is removed.

(14) A method of producing a carrier, wherein the carrier includes a protrusion provided thereon, and one or more and 100 or less types of allergens are immobilized on the protrusion(s) at a density of 120 ng/$cm^2$ or more and 500 ng/$cm^2$ or less, the method including the steps of:

immobilizing the allergen(s) on the protrusion(s) provided on the carrier; and quantifying the thus immobilized allergen(s) to measure the immobilization density of each allergen.

(15) The method of (14), wherein the allergen(s) is/are immobilized on the allergen-immobilization region(s) at a density of 180 ng/$cm^2$ or more and 300 ng/$cm^2$ or less.

Use of the carrier enables simultaneous measurement of multiple items of allergen-specific IgE antibodies using the amount of sample smaller than that used conventionally, with a high sensitivity and with a high correlation with "ImmunoCAP."

Figure 1:
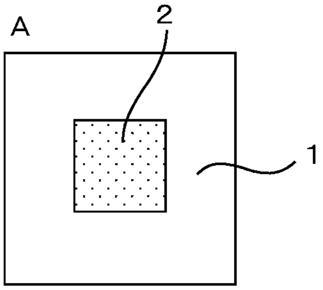
FIGS. 1A and 1B are diagrams showing examples of our carrier, in which a reaction vessel(s) is/are provided.
Figure 1:
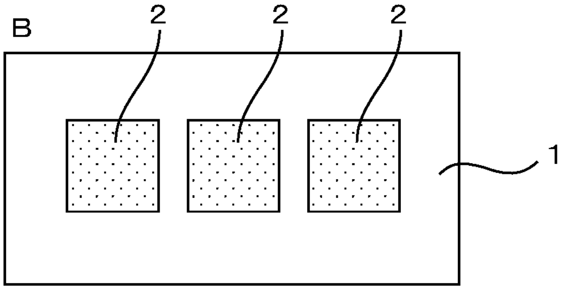

REFERENCE SIGNS LIST 1 carrier
2 reaction vessel
3 protrusion
4 allergen-immobilization region

DETAILED DESCRIPTION

The allergen-immobilized carrier is characterized in that the carrier includes an allergen-immobilization region on which the allergen is immobilized, and the allergen is immobilized at a density of 120 ng/$cm^2$ or more and 500 ng/$cm^2$ or less.

The allergen to be used is obtained by extracting a protein(s) contained in an allergenic raw material. The allergen may be extracted crude proteins, or may be those which have been further separated and purified, or a single isolated protein.

The "allergenic raw material" is a term that refers to a material containing an allergen that induces an allergy, in general. Specifically, the allergenic raw material may be, for example: a microorganism, a plant, an animal, an insect, mite or house dust; or food containing any of these. Whether or not an allergy is induced varies depending on the body constitution.

Examples of the microorganism containing an allergen include those belonging to genera *Alternaria, Aspergillus, Candida* and *Malassezia*. Examples of the plant containing an allergen include: Japanese cedar, Japanese cypress, Japanese alder, Japanese white birch, orchard-grass, ragweed, mugwort and timothy grass; and pollens of these plants. Examples of the animal containing an allergen include cats, dogs, mice, rats, hamsters, rabbits, parakeets and ducks. Examples of the insect containing an allergen include moths, cockroaches, bees and wasps. Examples of the food containing an allergen include egg, milk, wheat, peanut, soybean, soba, sesame seed, rice, shrimp, crab, squid, octopus, kiwi, banana, apple, peach, tomato, garlic, tuna, salmon, mackerel, beef, pork and chicken. In addition, examples of the material containing an allergen that causes an allergy in an outdoor environment include mite and house dust. Further, examples of the material containing a causative allergen for an occupational allergy include latexes.

It is possible to use a commercially available allergen or an allergen extracted from an allergenic raw material by oneself, as the allergen. The allergen can be extracted from an allergenic raw material by a known method, but not particularly limited thereto. The commercially available allergen can be purchased from Stallergenes Greer, Torii Pharmaceutical Co., Ltd., ITEA Inc., Cosmo Bio Co., Ltd., Biostir Inc. and the like.

Examples of the raw material of the allergen-immobilized carrier include resins, glass, metals, silicon wafers, ceramics, cellulose and nitrocellulose. In particular, resins which are inexpensive and have an excellent formability are desirable. Among the resins, a resin containing an aliphatic structure is preferred because the resin has less autofluorescence as compared to a resin containing an aromatic structure, and thus allows for noise reduction when used for a carrier for use in fluorescence detection analysis. Further, a resin containing an ester bond is preferred because a carboxyl group can be formed by a hydrolysis treatment, and the allergen can be immobilized by allowing the carboxyl group to form a covalent bond with an amino group contained in an allergenic protein. In particular, an acrylic resin is more preferred because the resin has an excellent workability, is compatible with various types of molding methods such as injection molding, extrusion molding and compression molding, and is also suitable for a processing such as machining, cutting, adhesion or bending. The acrylic resin may be, for example, a polyacrylate, a polymethacrylate, or a modified product thereof. In particular, a polymethacrylate is preferred. The polymethacrylate may be, for example, polymethyl methacrylate (PMMA), polyethyl methacrylate (PEMA), or a poly(alkyl methacrylate) (PAMA) such as poly(propyl methacrylate). In particular, PMMA which can be easily microfabricated by injection molding or hot embossing is preferred.

The acrylic resin to be used can also be a copolymer with an acrylic resin. For example, it is possible to use a copolymer containing a polymethacrylate such as a methyl methacrylate-acrylonitrile-butadiene-styrene copolymer (MABS resin), a methyl methacrylate-butadiene-styrene copolymer (MBS resin), methyl methacrylate-styrene copolymer (MS resin) or the like.

Alternatively, it is also possible to incorporate a black-colored substance into the acrylic resin. Preferred examples of the black-colored substance which can be used include carbon black, graphite, titanium black, aniline black, oxides of Ru, Mn, Ni, Cr, Fe, Co and Cu, and carbides of Si, Ti, Ta, Zr and Cr.

The shape of the carrier can be selected as appropriate from a plate-like shape, a thin film, particles, a porous form and the like. However, the carrier preferably has a plate-like shape.

The carrier preferably includes a protrusion, as the immobilization region on which the allergen is immobilized. When using a plate-like carrier, the protrusion as the allergen-immobilization region is preferably present on the upper surface of the carrier when the carrier is placed horizontally. Such an arrangement enables providing a number of protrusions that serve as the immobilization regions, on one piece of carrier.

As will be described later, the allergen-immobilized carrier is used to detect an allergen-specific IgE antibody. When detecting the allergen-specific IgE antibody bound to the carrier using a fluorescent-labeled secondary antibody, it is possible to employ a method of scanning the carrier using a scanner or the like. In such an example, if the carrier in which the allergen is immobilized on the upper surface(s) of the protrusion(s) is used, it is possible to obtain the effect that the fluorescence (noise) of the fluorescent-labeled secondary antibody non-specifically adsorbed on surfaces other than the protrusion(s) is hardly detected. The reason for this is because, since the irradiated light is focused on the upper surface(s) of the protrusion(s), the irradiated light is defocused on surfaces other than the upper surface(s) of the protrusion(s).

Each protrusion preferably has a flat upper surface. When each protrusion has a flat upper surface, an unevenness in fluorescence intensity does not occur within the upper surface of one protrusion, and a favorable signal (fluorescence) can be obtained.

When a plurality of protrusions are provided on the same carrier, the upper surfaces of the protrusions preferably have substantially the same area. Such an arrangement enables immobilizing equal amounts of allergen on the respective protrusions, in immobilizing the allergen on the entire surfaces of the respective protrusions. The expression that "the upper surfaces of the protrusions have substantially the same area" as used herein means that the value obtained by dividing the largest upper surface area of the protrusions, by the smallest upper surface area thereof, is 1.2 or less.

The area of the upper surface of the protrusion is preferably 4 $mm^2$ or less and 10 $\mu m^2$ or more, from the viewpoints that the amount of allergen used can be reduced, and of the ease of handling, but not particularly limited thereto. Each protrusion preferably has a height of 0.01 mm or more and 1 mm or less.

The plate-like carrier preferably includes an immobilization region on which the allergen is immobilized, and a reaction vessel that retains a sample such as a body fluid and allows the sample to react with the allergen. The reaction vessel may be, for example, a vessel in the form of a recess provided in the carrier, or a vessel formed on the carrier and surrounded by protruded partition walls.

FIGS. 1A and 1B show examples of the carrier including a reaction vessel(s). Each carrier 1 includes a reaction vessel(s) 2 for allowing a sample(s) to react with the allergen, and the reaction of the sample(s) can be performed in the reaction vessel(s) 2. Since the portion of the carrier outside the reaction vessel(s) does not come into contact with the sample(s), the portion outside the reaction vessel(s) can be prevented from being contaminated by the sample(s). A single reaction vessel may be present in one carrier as shown in FIG. 1A, or alternatively, one carrier may have a plurality of reaction vessels 2 as shown in FIG. 1B. In a carrier having a plurality of reaction vessels, the reactions of a plurality of samples can be performed separately in the respective reaction vessels in the same carrier. Therefore, is possible to simultaneously measure the plurality of samples accurately on the same carrier, while preventing the contamination between the samples.

Each reaction vessel includes an allergen-immobilization region on which the allergen is immobilized, and the immobilized allergen is brought into contact with a sample in the reaction vessel, to carry out the reaction. The allergen to be immobilized on the allergen-immobilization region may be one kind or two or more kinds. The reaction vessel may include a single allergen-immobilization region or a plurality of allergen-immobilization regions. When the reaction vessel includes a plurality of allergen-immobilization regions, the same allergen may be immobilized on all of the allergen-immobilization regions, or alternatively, two or more types of allergens may be respectively immobilized on separate allergen-immobilization regions. In the latter, it is possible to perform the detection of a plurality of types of allergen-specific antibodies in one reaction vessel and, thus, there is an advantage that the amount of sample required for a specific antibody test per one item of allergen can be reduced compared to a carrier in which one type of allergen-specific antibody can be detected in one reaction vessel.

Figure 2:
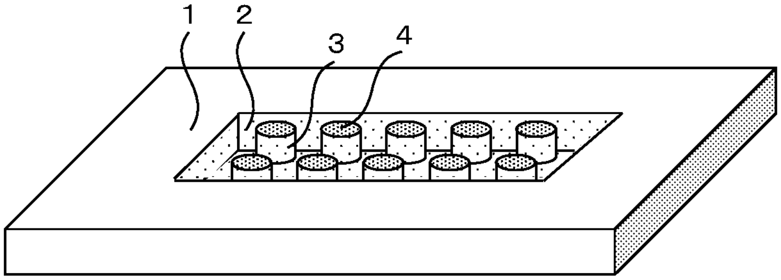
FIG. 2 is a diagram showing an example of our carrier provided with a reaction vessel having a plurality of protrusions on the upper surfaces of which an allergen(s) is/are immobilized.

FIG. 2 shows one example of the carrier in which a plurality of protrusions are provided in a reaction vessel, and the allergen is immobilized on the upper surfaces of the protrusions. A plurality of protrusions 3 are provided in a reaction vessel 2 in a carrier 1, and regions 4 on which the allergen is immobilized are formed on the upper surfaces of the protrusions. The allergen to be immobilized may be one kind, or two or more kinds. A resin carrier having a complex structure as that shown in FIG. 2 can be produced by injection molding.

The method of immobilizing the allergen on the carrier may be either immobilization by physical adsorption or immobilization by chemical bonding. However, immobilization by chemical bonding is preferred, because the allergen can be immobilized firmly. Immobilization by physical adsorption may be performed, for example, by a method using van der Waals force or hydrogen bonding. Specifically, the allergen can be physically adsorbed on the carrier, for example, by dropping a solution of the allergen on the carrier, and allowing the carrier to stand as it is, until the moisture is evaporated. Further, chemical immobilization may be performed, for example, by a method using covalent bonding, ionic bonding or coordinate bonding. Of these, a method using covalent bonding is preferred.

Immobilization of the allergen on a carrier made of a resin containing an ester such as an acrylic resin, by covalent bonding, can be achieved by forming a functional group capable of binding to the allergen, on the surface of the carrier. For example, the allergen can be immobilized by forming a carboxyl group on the carrier by a known method, and allowing the carboxyl group to form a covalent bond with an amino group contained in an allergenic protein. Specifically, the immobilization of the allergen can be achieved by: subjecting the surface of a carrier made of an acrylic resin such as PMMA to a hydrolysis treatment with an alkaline aqueous solution such as caustic soda, to form a carboxyl group on the resin surface, and then allowing the carboxyl group to directly form a covalent bond (amide bond) with an amino group contained in the extract of the allergen. Further, the immobilization of the allergen can also be achieved by introducing a maleimide group to the carboxyl group formed on the carrier by ester bonding, and allowing the maleimide group to form a covalent bond with a thiol group derived from a cysteine residue contained in the allergen. In addition, it is also possible to immobilize the allergen on a carrier made of an acrylic resin or the like, via a crosslinker such as DSG (disuccinimidyl glutarate), DSS (disuccinimidyl suberate), DSP (dithiobis(succinimidyl propionate)) or a water-soluble analog thereof, or a PEG (polyethylene glycol) linker, or alternatively, via a polymer shown below or the like.

The polymer which can be used for the immobilization of the allergen may specifically be, for example, a polymer containing a unit represented by formula (Ia) or formula (Ib).

$R^1$ in formula (Ia) and formula (Ib) represents an alkylene group having from 1 to 4 carbon atoms. $R^1$ is preferably a methylene group or an ethylene group, and more preferably a methylene group. $R^2$ in formula (Ia) represents $R^3$, $OR^4$ or $NHR^5$. Each of $R^3$ and $R^5$ independently represents a hydrogen atom or an alkyl group having from 1 to 4 carbon atoms, and $R^4$ represents an alkyl group having from 1 to 4 carbon atoms. $R^3$ is preferably a methyl group or an ethyl group, and more preferably a methyl group. $R^4$ is preferably a methyl group or an ethyl group, and more preferably a methyl group. $R^5$ is preferably a hydrogen atom. $R^6$ in formula (Ib) represents an alkylene group having from 1 to 2 carbon atoms. $R^6$ is preferably an ethylene group. Each of $R^7$ and $R^8$ in formula (Ib) independently represents a hydrogen atom or an alkyl group having from 1 to 4 carbon atoms. Each of $R^7$ and $R^8$ is preferably a hydrogen atom or a methyl group, and more preferably a hydrogen atom.

Further, the polymer which can be used for the immobilization of the allergen may be a heteropolymer containing a unit represented by formula (Ia) or (Ib), and a unit other than the unit represented by formula (Ia) or (Ib). When the polymer to be used for the immobilization is a heteropolymer, and the polymer is immobilized on the surface of a substrate by covalent bonding, the unit other than the unit represented by formula (Ia) or (Ib) preferably contains a reactive functional group. Examples of the reactive functional group include amino group, carboxyl group, hydroxy group, halogeno groups, tosyl group, epoxy group, acyl group and azido group. The reactive functional group is preferably an amino group.

In a heteropolymer, the ratio of the unit represented by formula (Ia) or (Ib) (sometimes collectively formula (I), for convenience) to the total unit is preferably 5% by mole or more and 95% by mole or less, more preferably 10% by mole or more and 90% by mole or less, and still more preferably 30% by mole or more and 70% by mole or less.

When the polymer containing a unit represented by formula (Ia) or (Ib) is a heteropolymer, the polymer is preferably a heteropolymer with a unit represented by formula (II). $R_1$ in formula (II) represents an alkylene group having from 1 to 4 carbon atoms, as in $R^1$ in formula (Ia) or (Ib).

Further, the ratio of the unit represented by formula (I), to the total of the unit represented by formula (I) and the unit represented by formula (II), in this heteropolymer, is preferably 5% by mole or more and 95% by mole or less, more preferably 10% by mole or more and 90% by mole or less, and still more preferably 30% by mole or more and 70% by mole or less:

(II)

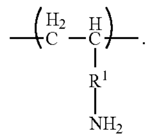

The application (spotting) of an allergen solution to the allergen-immobilization region(s) of the carrier can be carried out using a known spotting apparatus, dispenser, printer or the like. In immobilizing a plurality of types of allergens on the immobilization regions located close to each other, it is preferred to use a carrier in which a plurality of independent protrusions are provided in a reaction vessel and to apply the allergen solution to the upper surfaces of the protrusions as the allergen-immobilization regions to avoid different types of allergens to be mixed into adjacent allergen-immobilization regions because the allergen solution can be retained on the upper surfaces of the protrusions by surface tension. The plurality of protrusions in this example preferably have substantially the same height. The expression that "the protrusions have substantially the same height" means that the protrusions have such heights that, when the amounts of the substance to be tested bound to the upper surfaces of a plurality of protrusions having slightly different heights are measured by the fluorescence or the like using a scanner or the like, in a state where the same amounts of the substance are bound thereto, the difference in the measured values of the fluorescence intensity thereof or the like does not cause a problem. Specifically, "to have substantially the same height" means that the difference in height is less than 100 μm.

In our allergen-immobilized carrier, the allergen is immobilized on the allergen-immobilization region at a density of 120 $ng/cm^2$ or more and 500 $ng/cm^2$ or less. The immobilization density of the allergen is preferably 180 $ng/cm^2$ or more and 300 $ng/cm^2$ or less. The immobilization density is more preferably 190 $ng/cm^2$ or more and 280 $ng/cm^2$ or less, and still more preferably 195 $ng/cm^2$ or more and 270 $ng/cm^2$ or less.

The allergen can be immobilized at a predetermined immobilization density, for example, by a method in which the amount of allergen required for the surface area of the immobilization region is calculated; and the required amount of a solution of the allergen having a known concentration is applied to the entire immobilization region. At this time, the concentration of an allergenic protein, the reaction temperature and the reaction time can be selected as appropriate to carry out the immobilization, taking into consideration the reaction efficiency of the allergen immobilization via an amino group of the protein.

In performing the immobilization, for example, by the above-described method in which the allergen is physically adsorbed on the carrier by dropping a solution of the allergen on the carrier, and allowing the carrier to stand as it is, until the moisture is evaporated, it can be considered that the immobilization efficiency is almost 100%. Therefore, in using, for example, a carrier that includes a reaction vessel and a protrusion provided therein and in which the upper surface of the protrusion serves as the immobilization region, it is possible to produce a carrier in which the allergen is immobilized at a desired allergen immobilization density, by: calculating the amount of allergen required to achieve a desired immobilization density with respect to the area of the upper surface of the protrusion; applying a solution of the allergen containing the required amount thereof to the protrusion; and then leaving the carrier to stand overnight to allow moisture to dry.

In immobilizing the allergen to the carrier by covalent bonding, utilizing an amino group (amino group at the N-terminal or amino group in a lysine chain) of an allergenic protein, the efficiency of the immobilization reaction varies depending on the content of lysine included in the protein contained in each allergen, the three-dimensional structure of the protein and the like. Therefore, the allergen concentration, the reaction temperature and the reaction time are selected as appropriate, to produce the allergen-immobilized carrier. For example, in using a carrier made of an acrylic resin, which carrier includes a reaction vessel and a protrusion provided therein and in which the upper surface the protrusion serves as the immobilization region, and forming a carboxyl group on the surface of the carrier, to immobilize the allergen by covalent bonding, the allergen-immobilized carrier can be produced as follows. First, a carrier made of a resin containing an ester such as an acrylic resin, is prepared, the carrier is immersed in a 10 N aqueous solution of sodium hydroxide at 70° C. for 14 to 48 hours, to form a carboxyl group. The thus formed carboxyl group is converted to an NHS ester by a known method such as a method of allowing the carboxyl group to react with N-hydroxysuccinimide (NHS) and 1-ethyl-3-(3-dimethylaminopropyl)carbodiimide (EDC), and an allergen solution is added dropwise thereto to allow a condensation reaction with an amino group of an allergenic protein to occur. Since the inactivation of the NHS ester due to hydrolysis proceeds simultaneously with the condensation reaction with an amino group in the protein, a large excess, specifically, 100 times equivalent or more of the allergenic protein is usually used, and the reaction is allowed to proceed at room temperature roughly overnight. By washing the unbound allergenic protein with saline or the like, thereafter, it is possible to produce a carrier in which the allergen is immobilized at a density of 120 $ng/cm^2$ or more and 500 $ng/cm^2$ or less. The production of the carrier is preferably carried out by preparing a plurality of allergen solutions having a concentration within the range of from 0.01 to 50 mg/mL as appropriate, as to the amount of allergenic protein, with consideration to perform incubation under the conditions of a temperature of 1 to 37° C. for 1 to 48 hours, while estimating the reaction efficiency.

The quantification of the allergen immobilized on the carrier can be carried out by an indirect method in which the allergen immobilized on the carrier is released from the carrier to be collected in a liquid or the like, and then measured, or a method in which the allergen immobilized on the carrier is directly quantified, as it is.

The indirect quantification method may be, for example, a method in which the allergen immobilized on the carrier is released from the carrier to be collected in a liquid, and the concentration of the allergen in the liquid is measured by a known protein quantification method such as the ultraviolet spectrophotometric method, the BCA method, the Bradford method or the Lowry method. However, it is difficult to completely release the allergen firmly immobilized on the carrier, particularly such as one immobilized by covalent bonding. Therefore, in such an example, the following method in which the allergen on the carrier is directly quantified is preferred.

The method of directly quantifying the allergen immobilized on the carrier may be, for example, a method of labeling the allergenic protein on the carrier with a fluorescent substance, a radioactive isotope or the like, and measuring the intensity thereof. However, the labeling efficiency varies depending on the type of protein, for example, where it is not easy to accurately calculate the labeling efficiency. In such an example, it is preferred to employ a method of using time-of-flight secondary ion mass spectrometry (TOF-SIMS), and calculating the amount of immobilization from the intensity ratio of the peaks derived from the allergenic protein to the peaks derived from the resin of the carrier, in the resulting mass spectrum.

The method of detecting an allergen-specific antibody includes the steps of:

- bringing a sample into contact with the allergen-immobilized carrier described above, to form a complex of the allergen, and of an IgE antibody specific to the allergen contained in the sample; and
- detecting the thus formed complex of the allergen and the allergen-specific IgE antibody.

After the step of forming a complex of the allergen and the allergen-specific IgE anti-body, the step of washing the carrier to remove excessive sample components may be performed.

The step of detecting the thus formed complex can be performed by allowing a fluorescent-labeled secondary antibody that binds to the allergen-specific IgE antibody, to react therewith, and measuring the fluorescence intensity thereof. As the label of the secondary antibody, it is also possible to use an enzyme that produces a chromogenic or luminescent substance, a radioactive isotope or the like, in addition to a fluorescent substance (fluorescent pigment). However, a method of using a secondary antibody modified with a fluorescent substance which can be handled safely and easily, among those mentioned above, is preferred.

The sample to be used is preferably a sample derived from a body fluid. Examples of the body fluid include blood, sweat, urine, tear fluid, saliva, sputum/airway secretion, breast milk, amniotic fluid, cerebrospinal fluid, ascites, pleural effusion, joint fluid, semen and vaginal secretion. Of these, blood or tear fluid that contains large amounts of specific antibodies such as allergen-specific IgE antibodies, is preferred. In using blood, serum or plasma can also be preferably used. Further, the sample may be one subjected to a pretreatment, as necessary.

The pretreatment may be, for example, the dilution of the sample or the removal of a component(s) in the sample. The use of a diluted sample, or the use of a sample from which proteins or lipids other than the allergen-specific IgE antibody as the substance to be tested in the sample are removed, enables inhibiting non-specific adsorption reactions, and improving the detection sensitivity of the allergen-specific IgE antibody as the substance to be tested. Further, there are examples where IgG, IgM, IgA and IgD antibodies in a body fluid sample specifically bind to the allergen, to cause competitive inhibition in detecting the allergen-specific IgE antibody, possibly resulting in a decrease in the detection sensitivity of the allergen-specific IgE antibody. Therefore, it is preferred to use a sample from which at least one type of antibody (sometimes "non-IgE antibody") selected from the group consisting of IgG antibody, IgM antibody, IgA antibody and IgD antibody is removed.

Since the IgG antibody content is the highest in a body fluid sample, in particular, a pretreatment to remove IgG antibody is preferred to resolve the competition with the allergen-specific IgE antibody. The pretreatment of the sample may be, for example, filtration using a membrane, or chromatography such as affinity chromatography or ion-exchange chromatography. Specifically, the non-IgE antibodies in the sample can be adsorbed and removed by affinity chromatography using a carrier on which an antibody such as an anti-IgG antibody, an anti-IgM antibody, an anti-IgA antibody or an anti-IgD antibody, or alternatively, a known ligand such as protein A derived from *Staphylococcus aureus*, protein G derived from a group G hemolytic *Streptococcus*, protein L derived from a gram-positive anaerobic *coccus* or jacalin derived from jackfruit, is immobilized.

The allergen-immobilized carrier is produced by a method including the steps of: immobilizing the allergen on a protrusion provided on the carrier; and quantifying the thus immobilized allergen to measure the immobilization density of the allergen.

The step of immobilizing the allergen on a protrusion provided on the carrier can be carried out by the method described above. Specifically, the allergen may be immobilized by either immobilization by physical adsorption or immobilization by chemical bonding. However, immobilization by chemical bonding is preferred, because the allergen can be immobilized firmly. The chemical immobilization may be performed, for example, by a method using covalent bonding, ionic bonding or coordinate bonding. Of these, a method using covalent bonding is preferred.

The step of immobilizing the allergen on a protrusion provided on the carrier can be carried out by applying (spotting) a solution of the allergen to the allergen-immobilization region of the carrier. The application of the allergen solution can be carried out using a known spotting apparatus, dispenser, printer or the like.

The step of quantifying the thus immobilized allergen to measure the immobilization density of the allergen can be carried out by the method described above. Specifically, the step can be carried out by an indirect method in which the allergen immobilized on the carrier is released from the carrier to be collected in a liquid or the like, and then measured, or a method in which the allergen immobilized on the carrier is directly quantified, as it is. As the direct quantification method, it is possible to use a method of labeling the allergenic protein on the carrier with a fluorescent substance, a radioactive isotope or the like, and measuring the intensity thereof, as well as the TOF-SIMS method. The TOF-SIMS method is preferred.

Our production method enables determination of whether or not the allergen is immobilized at a predetermined immobilization density, and to perform quality control in the production process of the allergen-immobilized carrier.

EXAMPLES

Our carriers and methods will now be described in more specific detail, with reference to the following Examples.

Examples 1 to 6

(1) Production of Allergen-Immobilized Carrier (Carrier A)

(1)-1 Preparation of Carrier Made of NHS-Esterified PMMA

A substrate (75 mm×25 mm×1.0 mm) made of polymethyl methacrylate (PMMA) and provided with one reaction vessel (12.5 mm×10 mm×0.15 mm (depth)) including 256 protrusions (16×16, pitch: 560 μm) each in the form of a cone trapezoid whose upper surface has a diameter of 150 μm, as schematically shown in FIG. 2, was immersed in a 10 N aqueous solution of sodium hydroxide at 70° C. for 14 hours. Subsequently, the substrate was washed with pure water, a 0.1 N HCl aqueous solution and pure water, in the order mentioned. In this manner, the side chains of PMMA on the substrate surface were hydrolyzed, to form carboxyl groups.

Thereafter, 100 mg of N-hydroxysuccinimide (NHS) and 350 mg of 1-ethyl-3-(3-dimethylaminopropyl)carbodiimide (EDC) were dissolved in 400 mL of a 2-morpholinoethanesulfonic acid monohydrate (MES) buffer solution (adjusted to pH 5.0 with 0.1 N sodium hydroxide). The PMMA substrate which had been hydrolyzed as described above was immersed in the resulting mixed solution of the above compounds, followed by stirring the solution with a microstirrer for one hour, to obtain a PMMA substrate which had been NHS-esterified.

(1)-2 Preparation of Allergen Solutions

The egg white allergen used in Examples 1 and 2, and the milk allergen used in Examples 4 and 5, were obtained from Torii Pharmaceutical Co., Ltd., each as an allergen scratch extract. Since the allergen scratch extract contains 50% of concentrated glycerin, each extract was subjected to dialysis (dialysis membrane: Slide-A-Lyzer MINI Dialysis Device, 10K MWCO, dialysate: phosphate buffered saline) to remove glycerin, and then adjusted to the concentration shown in Table 1 with phosphate buffered saline, before use.

The egg white allergen and the milk allergen used in Example 3 and 6, obtained from an allergen manufacturer, Stallergenes Greer, are each in the form of a freeze-dried powder, and thus, each powder was dissolved in phosphate buffered saline and adjusted to 1.0 mg/mL, before use.

(1)-3 Immobilization of Allergens

The allergen solutions prepared in (1)-2 were respectively spotted on the upper surfaces of different protrusions on the NHS-esterified PMMA resin substrate prepared in (1)-1, using a spotting robot (GTMAS Stamp-2, manufactured by Japan Laser Electronics Co., Ltd.). Subsequently, the resulting substrate was placed in a sealed plastic container, and incubated under the conditions of a temperature of 37° C. and a humidity of 100% for 24 hours, to immobilize the allergens. After the incubation, the substrate was washed with phosphate buffered saline containing 0.05% Tween 20, to remove non-immobilized allergens. In this manner, "Carrier A" in which the egg white and milk allergens were respectively immobilized on the upper surfaces of different protrusions provided in one reaction vessel was obtained.

(2) Measurement of Allergen Immobilization Density

The egg white allergen solutions were each serially diluted with a mixed solvent of water and formamide to prepare standard solutions, the droplets thereof were dispensed on the PMMA substrates which are the same as that prepared in (1)-1, using a non-contact jet dispenser, Cyber Jet 2 (manufactured by Musashi Engineering Co., Ltd.), and naturally dried at room temperature until the solvent was evaporated. The allergen immobilization density was determined from the amount of the dispensed solution and the adhesion area of the dispensed solution, and 21 levels of standard substrates were prepared within the density range of from 0 to 400 ng/cm$^2$. The allergen-immobilization regions of the standard substrates were measured by TOF-SIMS (apparatus: TOF. SIMS 5 (manufactured by ION-TOF Inc.), primary ion species: $Bi_3^{++}$, primary ion acceleration voltage: 25 kV, pulse width: 11.7 ns, bunching: yes, measured vacuum level: $<4\times10^{-7}$ Pa, charge neutralization: yes, post-acceleration: 10 kV) to obtain positive secondary ion mass spectra, and calibration curves which allow for calculating the immobilization densities of the egg white allergens were prepared from the peak strength ratio of $C_4H_8N^+$ and $C_4H_5O^+$ in the thus obtained spectra.

The allergen-immobilization regions of Carrier A prepared in (1) were measured by TOF-SIMS under the same conditions, and the immobilization densities of the egg white allergens immobilized on the respective upper surfaces of the protrusions on Carrier A were calculated from the resulting peak strength ratio of $C_4H_8N^+$ and $C_4H_5O^+$, using the calibration curves (Examples 1 to 3).

In the same manner, calibration curves which allow for calculating the immobilization densities of the milk allergens were prepared, and the immobilization densities of the milk allergens immobilized on the respective upper surfaces of the protrusions on Carrier A were calculated, using the thus prepared calibration curves (Examples 4 to 6).

Results are shown in Table 1.

(3) Evaluation of Correlation with "ImmunoCAP"

Using Carrier A prepared in (1), the fluorescence intensities of allergy positive and allergy negative samples were measured by the following method, and the allergen-specific antibody in each sample was measured. A total of seven samples (plasma) negative and positive for egg white, milk, peanut and mite allergy, which had been purchased from PlasmaLab International and whose ImmunoCAP values are known, were used as the samples.

The ImmunoCAP values in the same samples were plotted on the X axis, and the measured fluorescence intensities were plotted on the Y axis, and the correlation coefficient R between both values was calculated.

The results are shown in Table 1.

In the above operation, the measurement of the above-described allergen-specific antibody (fluorescence intensity) was carried out as follows.

Carrier A prepared in (1) was immersed in Blocking Reagent For ELISA (manufactured by Sigma-Aldrich Co. LLC.) overnight at 4° C. to perform a blocking treatment, and then washed three times with PBST. A quantity of 50 μL of a solution obtained by diluting each sample three-fold with phosphate buffered saline was dropped on the parts of the carrier after the above-described treatment on which the allergens had been immobilized, and a gap cover glass (24 mm×25 mm, gap size: 20 μm; manufactured by Matsunami Glass industries Ltd.) was placed thereover and sealed. After allowing the reaction to proceed for two hours at 37° C., the gap cover glass was removed, and washed three times with PBST. Subsequently, 50 μL of Dylight 650-labeled anti-human IgE goat polyclonal antibody (manufactured by Novus biologicals, Inc.) which had been diluted 1000-fold with PBST containing 1% by weight BSA was added to the substrate, a gap cover glass was placed thereover, and the reaction was allowed to proceed at room temperature for one hour. Thereafter, the gap cover glass was removed, the substrate was washed three times with PBST, followed by drying, and the fluorescence intensity measurement was carried out using a scanning apparatus (3D-Gene Scanner 3000, manufactured by Toray Industries, Inc.) under the following conditions:

Conditions for Measuring Fluorescence Intensity

Apparatus: 3D-Gene Scanner 3000 (manufactured by Toray Industries, Inc.)
Exciting light wavelength: 635 nm
Detection wavelength: 670 nm
PMT: 30.

(4) Measurement of Allergen-Specific IgE in Negative Sample and Positive Sample

The fluorescence intensities of the following negative sample A and positive sample B were measured, using Carrier A prepared in (1) and by the same method as in (3) described above, and egg white allergen-specific antibody (Example 1 to 3) and milk allergen-specific antibody (Example 4 to 6) were detected.

The samples used were both plasma samples purchased from PlasmaLab International. A sample which is negative for all of egg white, milk, peanut and mite allergies, that is, a negative sample A which is Class 0 in all of the egg white allergy class, the milk allergy class, the peanut allergy class and the mite allergy class (egg white-specific IgE concentration: less than 0.1 IU/mL, milk-specific IgE concentration: less than 0.1 IU/mL, peanut-specific IgE concentration: less than 0.1 IU/mL, mite-specific IgE concentration: less than 0.1 IU/mL); and a positive sample B which is Class 1 in both the egg white allergy class and the milk allergy class (egg white-specific IgE concentration: 0.38 IU/mL, milk-specific IgE concentration: 0.62 IU/mL); were used. Each allergy class is divided into 7 levels including Class 0 which is negative, and Class 1 to Class 6 which are positive, and a higher specific IgE concentration indicates a higher allergy class. A sample with a specific IgE antibody concentration of less than 0.35 is negative, and defined as Class 0. A sample with a specific IgE antibody concentration of 0.35 or more is positive, and a sample with a specific IgE antibody concentration of 0.35 or more and less than 0.70 is defined as Class 1. A higher specific IgE antibody concentration indicates a higher class.

The fluorescence intensities of the negative sample A and the positive sample B were measured, and the ratio (positive sample/negative sample) of the fluorescence intensity of the positive sample B to the fluorescence intensity of the negative sample A was calculated. The results are shown in Table 1.

Examples 7 to 11

The items of the allergens, the manufacturers of the allergens, the concentrations of the allergens and the incubation times were set as shown in Table 1, and "Carrier B" in which the egg white and milk allergens were respectively immobilized on the upper surfaces of different protrusions provided in one reaction vessel was prepared, in the same manner as in Examples 1 to 6. Thereafter, the measurement of the allergen immobilization density, the evaluation of the correlation with "ImmunoCAP," and the measurement of allergen-specific IgE were carried out for each Example.

The results are shown in Table 1.

Example 12 and Comparative Example 1

The items of the allergens, the manufacturers of the allergens, the concentrations of the allergens and the incubation times were set as shown in Table 1, and "Carrier C" in which the egg white and milk allergens were respectively immobilized on the upper surfaces of different protrusions provided in one reaction vessel was prepared, in the same manner as in Examples 1 to 6. Thereafter, the measurement of the allergen immobilization density, the evaluation of the correlation with "ImmunoCAP," and the measurement of allergen-specific IgE were carried out for the Example and the Comparative Example.

The results are shown in Table 1.

TABLE 1

| | Allergen immobilization conditions | | | | | Allergen Immobilization density $ng/cm^2$ | Correlation coefficient R | Fluorescence intensity ratio Class 1 positive sample B/Class 0 negative sample A |
|---|---|---|---|---|---|---|---|---|
| | Items | Manufacturer | Concentration mg/mL | Time h | Carrier | | | |
| Example 1 | Egg white | Torii Pharmaceutical | 0.5 | 24 | Carrier A | 196 | 0.90 | 2.5 |
| Example 2 | Egg white | Torii Pharmaceutical | 1.0 | 24 | | 219 | 0.96 | 2.9 |
| Example 3 | Egg white | GREER | 1.0 | 24 | | 220 | 0.91 | 4.4 |
| Example 4 | Milk | Torii Pharmaceutical | 0.2 | 24 | | 192 | 0.96 | 3.8 |
| Example 5 | Milk | Torii Pharmaceutical | 0.5 | 24 | | 225 | 0.95 | 3.7 |
| Example 6 | Milk | GREER | 1.0 | 24 | | 230 | 0.99 | 3.8 |
| Example 7 | Egg white | Torii Pharmaceutical | 2.0 | 16 | Carrier B | 241 | 0.93 | 3.6 |
| Example 8 | Milk | Torii Pharmaceutical | 1.0 | 16 | | 266 | 0.96 | 4.5 |
| Example 9 | Egg white | Torii Pharmaceutical | 0.2 | 16 | | 170 | 0.71 | 2.1 |
| Example 10 | Egg white | Torii Pharmaceutical | 4.0 | 16 | | 317 | 0.96 | 1.6 |
| Example 11 | Milk | Torii Pharmaceutical | 0.2 | 16 | | 163 | 0.95 | 1.7 |
| Comparative Example 1 | Egg white | Torii Pharmaceutical | 1.0 | 4 | Carrier C | 113 | 0.54 | 0.9 |
| Example 12 | Milk | Torii Pharmaceutical | 3.0 | 4 | | 327 | 0.96 | 1.7 |

Examples 13 to 15 and Comparative Examples 2 to 4

The items of the allergens, the manufacturers of the allergens, the concentrations of the allergens and the incubation times were set as shown in Table 2, and "Carrier D" in which the egg white, milk, peanut and mite allergens were respectively immobilized on the upper surfaces of different protrusions provided in one reaction vessel was prepared, in the same manner as in Examples 1 to 6. Thereafter, the measurement of the allergen immobilization density, the evaluation of the correlation with "ImmunoCAP," and the measurement of allergen-specific IgE were carried out for each of the Examples and Comparative Examples.

The peanut allergen used in Example 13 was obtained from Torii Pharmaceutical Co., Ltd., as an allergen scratch extract. Since the allergen scratch extract contains 50% of concentrated glycerin, the extract was subjected to dialysis (dialysis membrane: Slide-A-Lyzer MINI Dialysis Device, 10K MWCO, dialysate: phosphate buffered saline) to remove glycerin, and then adjusted to the concentration shown in Table 2 with phosphate buffered saline, before use.

The mite allergen used in Examples 14 and 15 obtained from an allergen manufacturer, Stallergenes Greer, and the mite allergen used in Comparative Example 4 obtained from Biostir Inc. are each in the form of a freeze-dried powder, and thus, each powder was dissolved in phosphate buffered saline and adjusted to the concentration shown in Table 2, before use.

In the measurement of allergen-specific IgE, the negative sample A and a positive sample C were used. The fluorescence intensities of the negative sample A and the positive sample C were measured, and the ratio (positive sample/negative sample) of the fluorescence intensity of the positive sample C to the fluorescence intensity of the negative sample A was calculated. The results are shown in Table 2. The positive sample C is a plasma sample purchased from PlasmaLab International, and is a sample which is Class 1 in all of the egg white allergy class, the milk allergy class, the peanut allergy class and the mite allergy class (egg white-specific IgE concentration: 0.39 IU/mL, milk-specific IgE concentration: 0.50 IU/mL, peanut-specific IgE concentration: 0.39 IU/mL, mite-specific IgE concentration: 0.38 IU/mL).

The results are shown in Table 2.

Examples 16 to 20, and Comparative Examples 5 and 6

The items of the allergens, the manufacturers of the allergens, the concentrations of the allergens and the incubation times were set as shown in Table 2, and "Carrier E" in which the egg white, milk, peanut and mite allergens were respectively immobilized on the upper surfaces of different protrusions provided in one reaction vessel was prepared, in the same manner as in Examples 13 to 15 as well as Comparative Examples 2 to 4. Thereafter, the measurement of the allergen immobilization density, the evaluation of the correlation with "ImmunoCAP," and the measurement of allergen-specific IgE were carried out for each of the Examples and Comparative Examples.

The peanut allergen used in Example 17, obtained from an allergen manufacturer, Stallergenes Greer, is in the form of a freeze-dried powder, and thus, the powder was dissolved in phosphate buffered saline and adjusted to the concentration shown in Table 2, before use.

The results are shown in Table 2.

Examples 21 to 24 and Comparative Examples 7 to 9

The items of the allergens, the manufacturers of the allergens, the concentrations of the allergens and the incubation times were set as shown in Table 2, and "Carrier F" in which the egg white, milk, peanut and mite allergens were respectively immobilized on the upper surfaces of different protrusions provided in one reaction vessel was prepared, in the same manner as in Examples 13 to 15 as well as Comparative Examples 2 to 4. Thereafter, the measurement of the allergen immobilization density, the evaluation of the correlation with "ImmunoCAP," and the measurement of allergen-specific IgE were carried out for each of the Examples and Comparative Examples.

The results are shown in Table 2.

TABLE 2

| | Allergen immobilization conditions | | | | | Allergen immobilization | | Fluorescence intensity ratio Class 1 positive |
|---|---|---|---|---|---|---|---|---|
| | Items | Manufacturer | Concentration mg/mL | Incubation Time h | Carrier | density ng/cm$^2$ | Correlation coefficient R | sample C/Class 0 negative sample A |
| Comparative Example 2 | Egg white | Torii Pharmaceutical | 8.0 | 24 | Carrier D | 700 | 0.75 | 1.2 |
| Comparative Example 3 | Milk | Torii Pharmaceutical | 10.0 | 24 | | 515 | 0.97 | 1.4 |
| Example 13 | Peanut | Torii Pharmaceutical | 0.25 | 24 | | 150 | 0.98 | 1.6 |
| Example 14 | Mite | GREER | 0.1 | 24 | | 184 | 0.99 | 2.5 |
| Example 15 | Mite | GREER | 0.7 | 24 | | 336 | 0.78 | 2.6 |
| Comparative Example 4 | Mite | Biostir | 4.0 | 24 | | 562 | 0.77 | 1.1 |
| Comparative Example 5 | Egg white | Torii Pharmaceutical | 0.1 | 16 | Carrier E | 110 | 0.64 | 1.0 |
| Comparative Example 6 | Egg white | Torii Pharmaceutical | 10.0 | 16 | | 527 | 0.75 | 0.4 |
| Example 16 | Milk | Torii Pharmaceutical | 0.1 | 16 | | 135 | 0.89 | 3.2 |
| Example 17 | Peanut | GREER | 3.0 | 16 | | 207 | 0.99 | 2.3 |
| Example 18 | Peanut | Torii Pharmaceutical | 4.0 | 16 | | 291 | 0.99 | 2.1 |
| Example 19 | Peanut | Torii Pharmaceutical | 8.0 | 16 | | 388 | 0.86 | 2.3 |
| Example 20 | Mite | GREER | 0.2 | 16 | | 152 | 0.75 | 2.6 |
| Example 21 | Egg white | GREER | 8.0 | 4 | Carrier F | 315 | 0.96 | 1.8 |
| Example 22 | Egg white | Torii Pharmaceutical | 10.0 | 4 | | 327 | 0.96 | 1.6 |
| Example 23 | Milk | Torii Pharmaceutical | 8.0 | 4 | | 343 | 0.96 | 1.8 |
| Comparative Example 7 | Milk | Torii Pharmaceutical | 0.1 | 4 | | 16 | 0.64 | 1.0 |
| Comparative | Peanut | Torii | 0.25 | 4 | | 64 | 0.45 | 1.5 |

TABLE 2-continued

| | Allergen immobilization conditions | | | | | Allergen immobilization | | Fluorescence intensity ratio Class 1 positive |
|---|---|---|---|---|---|---|---|---|
| | Items | Manufacturer | Concentration mg/mL | Incubation Time h | Carrier | density ng/$cm^2$ | Correlation coefficient R | sample C/Class 0 negative sample A |
| Example 8 | | Pharmaceutical | | | | | | |
| Example 24 | Mite | Biostir | 4.0 | 4 | | 204 | 0.98 | 2.4 |
| Comparative Example 9 | Mite | GREER | 0.7 | 4 | | 92 | 0.65 | 1.5 |

As can be seen from the results of Examples 1 to 24, the correlation coefficient R was 0.7 or more for all allergens, in the allergen-immobilized carrier, indicating a high correlation with "ImmunoCAP."

In Examples 1 to 8, 10 to 14, 17, 18 and 21 to 24, the correlation coefficient R was 0.9 or more for all allergens, indicating an even higher correlation with "ImmunoCAP."

The allergens immobilized on allergen-immobilized carriers in allergy test drugs are obtained by extracting proteins contained in allergenic raw materials, and the allergenic raw materials are derived from nature in many examples. Therefore, it has been difficult to realize tests that have a high correlation with "ImmunoCAP," due to individual differences in allergenic raw materials, differences in collection methods as well as differences in extraction conditions. We found that our allergen-immobilized carrier enables achievement of a high correlation with "ImmunoCAP," even when using samples obtained from different allergen manufacturers such as Torii Pharmaceutical Co., Ltd., Stallergenes Greer and Biostir Inc., and even when individual allergenic raw materials and extraction conditions are different.

Further, in Examples 1 to 24, the fluorescence intensity ratio of Class 1 sample to Class 0 sample, which samples are at the boundary between negative and positive, was not less than 1.5 times for all allergens, indicating that the allergen-immobilized carrier enables performing an accurate allergy testing with a high sensitivity.

In Examples 1 to 9, 14 to 20 and 24, the fluorescence intensity ratio of Class 1 sample to Class 0 sample, which samples are at the boundary between negative and positive, was not less than 2 times for all allergens, indicating that it is possible to perform an accurate allergy testing with an even higher sensitivity.

As can be seen from the results of Examples 1 to 24, the use of the carrier enables obtaining a high correlation with "ImmunoCAP," achieving a correlation coefficient R of 0.7 or more, and also to perform an accurate measurement with a high sensitivity, achieving a fluorescence intensity ratio of Class 1 sample to Class 0 sample of not less than 1.5 times. Further, as can be seen from the results of Examples 1 to 8, 14, 17, 18 and 24, the use of a carrier in which each allergen is immobilized at a density of 180 ng/$cm^2$ or more and 300 ng/$cm^2$ or less enables obtaining an even higher correlation with "ImmunoCAP," achieving a correlation coefficient R of 0.9 or more, and also to perform an accurate measurement with an even higher sensitivity, achieving a fluorescence intensity ratio of Class 1 sample to Class 0 sample of not less than 2 times.

As can be seen from the results of Comparative Examples 1 to 9, on the other hand, it has been revealed that a carrier with an allergen immobilization density of lower than 120 ng/$cm^2$ or a carrier with an allergen immobilization density of higher than 500 ng/$cm^2$ cannot achieve both obtaining a correlation coefficient of 0.7 or more and being able to perform a measurement with a fluorescence intensity ratio of Class 0 sample to Class 1 sample of not less than 1.5 times.

Further, in each of Carriers A, B, D, E and F used for Examples 1 to 11 and 13 to 24, a plurality of allergens (two or more types of egg white, milk, peanut and mite allergens) are immobilized on the upper surfaces of a plurality of protrusions provided in one reaction vessel, and the measurements of a plurality of types of allergen-specific IgE antibodies were carried out simultaneously using each of these carriers. The results have revealed that the use of the carrier enables simultaneously performing accurate measurements of multiple items of allergens, with a high correlation with "ImmunoCAP" and with a high sensitivity.

The invention claimed is:

1. An allergen-immobilized carrier for detecting an allergen-specific antibody, wherein said carrier comprises at least one allergen-immobilization region on which said allergen is immobilized; and said allergen is immobilized at a density of 180 ng/$cm^2$ or more and 300 ng/$cm^2$ or less.

2. The allergen-immobilized carrier of claim 1, wherein said carrier comprises a protrusion provided thereon, and said protrusion is said allergen-immobilization region.

3. The allergen-immobilized carrier of claim 1, wherein two or more and 100 or less types of allergens are immobilized on said at least one allergen-immobilization regions.

4. The allergen-immobilized carrier of claim 1, wherein said allergen(s) is/are immobilized via a polymer comprising a unit represented by formula (Ia) or (Ib):

(Ia)

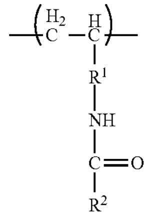

(Ib)

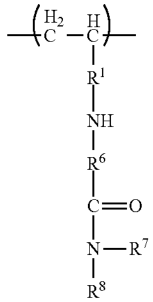

wherein, in formula (Ia) and formula (Ib), $R^1$ represents an alkylene group having from 1 to 4 carbon atoms; $R^2$ represents $R^3$, $OR^4$ or $NHR^5$, wherein each of $R^3$ and $R^5$ independently represents a hydrogen atom or an alkyl group having from 1 to 4 carbon atoms, and $R^4$ represents an alkyl group having from 1 to 4 carbon atoms; $R^6$ represents an alkylene group having from 1 to 2 carbon atoms; and each of $R^7$ and $R^8$ independently represents a hydrogen atom or an alkyl group having from 1 to 4 carbon atoms.

5. The allergen-immobilized carrier of claim 2, wherein said carrier comprises a reaction vessel including said protrusion provided thereon.

6. The allergen-immobilized carrier of claim 1, wherein at least one of said allergen(s) is egg white, milk, peanut or mite.

7. The allergen-immobilized carrier of claim 1, wherein said carrier is made of a resin containing an aliphatic structure.

8. The allergen-immobilized carrier of claim 1, wherein said carrier is made of a resin containing an ester.

9. The allergen-immobilized carrier of claim 1, wherein said carrier is made of an acrylic resin.

10. The allergen-immobilized carrier of claim 1, wherein said carrier is made of a polyacrylate or a polymethacrylate.

11. A method of detecting an allergen-specific antibody, the method comprising the steps of:

bringing a sample into contact with the allergen-immobilized carrier of claim 1, to form a complex of said allergen, and of an IgE antibody specific to said allergen contained in said sample; and detecting the thus formed complex of said allergen and said allergen-specific IgE antibody.

12. The method of detecting an allergen-specific antibody of claim 11, wherein said sample is a sample from which at least one type of antibody selected from the group consisting of IgG antibody, IgM antibody, IgA antibody and IgD antibody is removed.

13. A method of producing a carrier, wherein said carrier comprises a protrusion provided thereon, and one or more and 100 or less types of allergens are immobilized on said protrusion(s) at a density of 180 $ng/cm^2$ or more and 300 $ng/cm^2$ or less, said method comprising the steps of:

immobilizing said allergen(s) on said protrusion(s) provided on said carrier; and quantifying the thus immobilized allergen(s) to measure the immobilization density of each allergen.

* * * * *